United States Patent [19]

Ballard

[11] Patent Number: 5,709,746
[45] Date of Patent: Jan. 20, 1998

[54] SELF-CONTAINED FINGERPRINT KIT

[75] Inventor: Patricia A. Ballard, Manchester, N.H.

[73] Assignee: Moore Business Forms, Inc., Grand Island, N.Y.

[21] Appl. No.: 669,935

[22] Filed: Jun. 25, 1996

[51] Int. Cl.$^6$ .................................................. B05C 19/00
[52] U.S. Cl. .............................. 118/31.5; 118/264; 427/1
[58] Field of Search ..................... 118/31.5, 264; 427/1

[56] References Cited

U.S. PATENT DOCUMENTS

| | | |
|---|---|---|
| 1,322,293 | 11/1919 | Effrig . |
| 1,380,506 | 6/1921 | Voght . |
| 1,483,926 | 2/1924 | Chadwick et al. . |
| 2,500,612 | 3/1950 | Krogh . |
| 3,467,055 | 9/1969 | Yonchar ........................... 118/31.5 |
| 3,664,910 | 5/1972 | Hollie ............................. 118/31.5 |
| 3,709,524 | 1/1973 | McKee . |
| 3,720,304 | 3/1973 | Laugherty et al. . |
| 3,867,164 | 2/1975 | Orlando et al. .................. 118/31.5 |
| 4,699,077 | 10/1987 | Meadows et al. . |
| 4,943,089 | 7/1990 | Reardon . |
| 5,009,919 | 4/1991 | Vassiliades . |
| 5,143,551 | 9/1992 | Mason, Jr. et al. . |
| 5,253,798 | 10/1993 | Lombardo . |
| 5,314,110 | 5/1994 | Lombardo . |
| 5,330,231 | 7/1994 | Godfrey . |
| 5,601,867 | 2/1997 | Riedl et al. ..................... 118/31.5 |

FOREIGN PATENT DOCUMENTS

| | | |
|---|---|---|
| 2 119 314 | 11/1983 | United Kingdom . |
| 8601392 | 3/1986 | WIPO ............................... 427/1 |

OTHER PUBLICATIONS

"I.D. Print" brochure, ID Identicator Corporation, 1994.
Smith & Wesson "Identa-Print" Inkless Fingerprinting System Brochure, 1995.
Ident-A-Print Document Protection System sample Not Negotiable check, 1995.
Child identification card, 1995.
Identaprint Security Identification System, 1995.
Rapids Identification Card, 1995.

*Primary Examiner*—Laura Edwards
*Attorney, Agent, or Firm*—Nixon & Vanderhye P.C.

[57] ABSTRACT

A self-contained fingerprint kit includes first, second, and third (or more) panels each having a top face and a bottom face with panel joining adhesive along the exterior edges of at least some of the panel faces for holding them together so that the top face of the second panel engages the bottom face of the first panel, and the bottom face of the second panel engages the top face of the third panel. A first dry fingerprint chemical is disposed in an area provided on one of the first panel bottom face or the second panel top face, and a fingerprint application area (which may comprise a second dry fingerprint chemical which cooperates with the first chemical to provide a developed fingerprint) provided on the second bottom panel face or the third panel top face for receipt of fingerprints with fingerprint chemical transferred from a first dry fingerprint chemical. A photograph-receiving adhesive area is preferably provided on the second panel with a release liner covering the adhesive area, the adhesive area large enough to mount a photograph. The panels may be made by folding a substantially quadrate sheet of paper (e.g. 8½×11 inch bond paper) and sealing the adhesive joining the panels together with pressure so as to not adversely affect the fingerprint chemical. The integral kit may be disposed in a box of cereal or otherwise packaged for consumer use.

19 Claims, 4 Drawing Sheets

FIG. 5
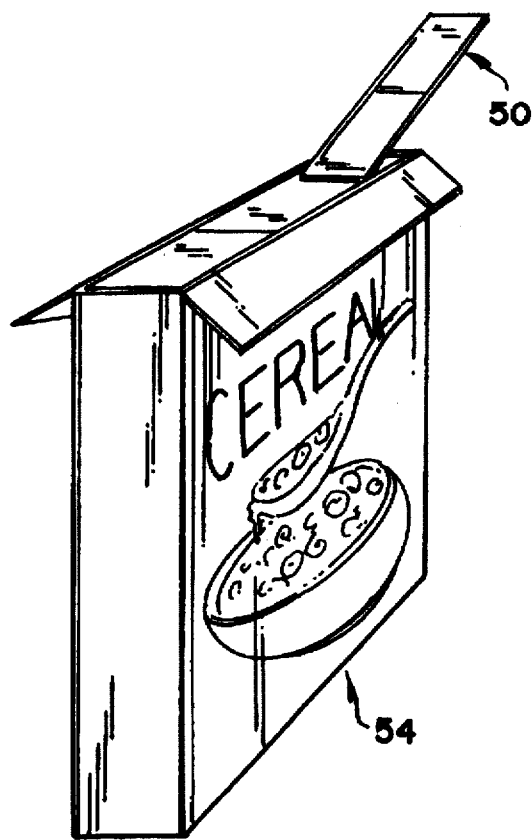
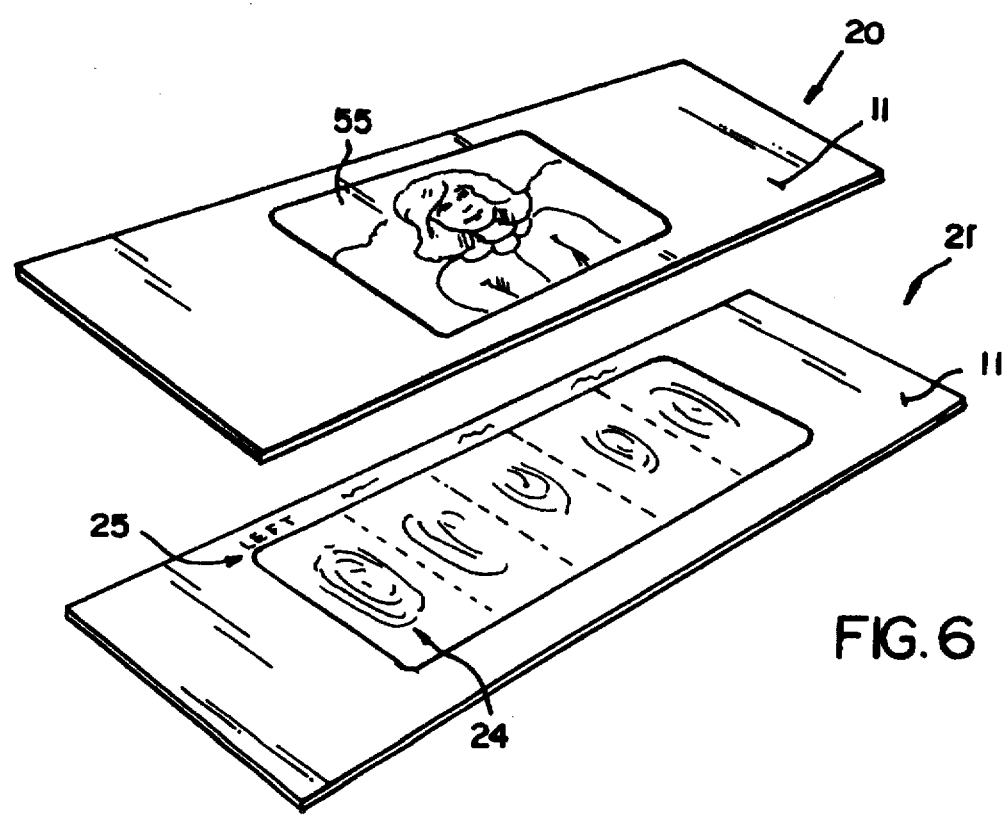
FIG. 6

SELF-CONTAINED FINGERPRINT KIT

BACKGROUND AND SUMMARY OF THE INVENTION

There is a commonly recognized desire to obtain and retain in a safe place information that uniquely identifies an individual (particularly children) in case that individual is ever missing or injured and needs to be found or identified. In particular a number of commercial systems have been developed for quickly and easily fingerprinting individuals, such as family members, for subsequent identification purposes. Other commercial systems are provided for utilizing fingerprints for document protection systems, or for associating individuals by photographs and/or fingerprint, with negotiable instruments. While a wide variety of such systems are provided, oftentimes they have complexities, lack of versatility and/or expense that limit their applicability to a number of different situations.

According to the present invention a self-contained fingerprint kit is provided which is simple, easy, and inexpensive to construct, in fact being so inexpensive and easy to utilize that it may be used for promotional purposes, for example contained in boxes of cereal. The self-contained fingerprint kit according to the invention positively segregates fingerprint developing chemicals associated therewith from the surroundings (such as the contents of a box of cereal) yet allows ready access to a fingerprint, chemical or chemicals, and makes it simple and easy for any member of the public to easily take fingerprints and to make a permanent record of the fingerprints, and even to associate them with a photograph. The invention also allows the unnecessary components to be easily detached and discarded. Thus, the self-contained fingerprint kit according to the present invention is ideally suited for use by parents in fingerprinting, and associating the fingerprints with a photograph with, their children, and despite its utility the self-contained fingerprint kit according to the invention is simple and easy to make and use, and inexpensive.

According to one aspect of the present invention a self-contained fingerprint kit is provided comprising the following components: First, second and third panels, each having a top face and a bottom face. Panel joining adhesive for holding the panels together so that the top face of the second panel engages the bottom face of the first panel, and the bottom face of the second panel engages the top face of the third panel, the panels substantially parallel to each other. A first dry fingerprint chemical disposed in an area provided on one of the first panel bottom face or the second panel top face. And a fingerprint application area provided on the second panel bottom face, or the third panel top face, for receipt of fingerprints with fingerprint chemical transferred from the first dry fingerprint chemical.

Typically, the first, second and third panels are formed of cellulose stock, such as bond paper, and are connected to each other by lines of weakness, such as perforation lines, so that the panels may be readily separable from each other. The fingerprint application area may comprise a second dry fingerprint chemical disposed thereon, the first and second fingerprint chemicals cooperating to provide the developed fingerprint. Most desirably the first dry fingerprint chemical area is disposed on the first panel bottom face and the second dry fingerprint chemical area is disposed on a third panel top face, and a photograph-receiving adhesive area is preferably disposed on the second panel bottom face. A release liner covers the adhesive area, and the adhesive area is large enough to mount a photograph thereon.

Typically the panels are quadrate and of substantially the same size (e.g. each formed from a sheet having a width of about 8½ inches and a length of about 11 inches), having aligned end edges and side edges. The panel joining adhesive must be such that when activated it does not interfere with the fingerprint chemicals, or in any way cause them to degrade. Preferably the panel joining adhesive comprises pressure sensitive adhesive or coadhesive, such as conventionally used by Moore Business Forms, Inc. in pressure seal mailers, including Z-fold mailers, and such as illustrated and described in U.S. Pat. Nos. 5,253,798 and 5,314,110 (the disclosures of which are hereby incorporated by reference herein). The adhesive is separated from the first and second fingerprint chemical areas and the photograph-receiving adhesive area by lines of weakness. The kit, when its construction is completed, is substantially completely sealed so that the dry fingerprint chemicals will not flake, migrate, or otherwise move from the kit to the surrounding environment, so that the kit may be disposed within, and be in combination, a box of cereal.

Typically, for example, the first and second dry, inkless, fingerprint chemicals may be those commercially available from the Scott Company of Flower Mound, Tex., the first chemical being water soluble so that when touched by a wet human finger will transfer to the finger, and then can be applied to the second dry fingerprint chemical to develop a fingerprint.

According to another aspect of the present invention a substantially quadrate sheet of paper per se is provided (which is typically utilized to make the self-contained fingerprint kit as described above). This substantially quadrate sheet of paper has the following characteristics: Substantially parallel and opposite first and a second major faces, first and second substantially parallel end edges, and first and second substantially parallel side edges substantially perpendicular to the end edges. At least first and second lines of weakness substantially parallel to the end edges and separating the sheet into at least first, second, and third panels. A first dry fingerprint chemical disposed on the second face. And a fingerprint receiving area disposed on the first face.

Preferably the first dry fingerprint chemical is disposed on the first panel and the fingerprint receiving area is disposed on the third panel, and the fingerprint receiving area comprises a second dry fingerprint chemical cooperating with the first chemical when applied thereto by a human finger to develop a fingerprint. Preferably the panels are substantially the same size, and the lines of weakness are perforation lines, although they alternatively may be fold lines, crease lines, score lines, die cut lines, or the like. A photograph-receiving adhesive area is preferably provided on the first face in the second panel, and a release sheet covers the photograph-receiving area. The adhesive is pressure sensitive adhesive, preferably a conventional permanent pressure sensitive adhesive. The sheet may also have third and fourth lines of weakness substantially parallel to and adjacent the first and second side edges to define marginal areas, and pressure sensitive adhesive or coadhesive may be disposed in the marginal areas (as well as along one of the end edges).

According to yet another aspect of the present invention a self-contained fingerprint kit is provided comprising the following components: First, second and third panels, each having a top face and a bottom face. A first dry fingerprint chemical disposed in an area provided on one of the first panel bottom face or the second panel top face. And a fingerprint application area provided on the second panel bottom face, or the third panel top face, comprising a second dry fingerprint chemical disposed thereon, the second chemical for cooperating with the first chemical when applied thereto by a human finger to develop a fingerprint. Preferably a photograph-receiving adhesive area is provided on the second panel bottom face, and a release liner covers the pressure sensitive adhesive, the adhesive area large enough to mount a photograph thereon.

It is a primary object of the present invention to provide a simple, inexpensive, yet effective self-contained fingerprint kit, and a sheet of paper utilizable to readily construct such a kit. This and other objects of the invention will become clear from an inspection of the detailed description of the invention and from the appended claims.

BRIEF DESCRIPTION OF THE DRAWINGS

FIG. 5 is a front perspective schematic view illustrating insertion of a fingerprint kit according to the present invention into a box of cereal to be provided in combination therewith; and FIG. 6 is a top perspective view of the panels of the fingerprint kit according to the present invention that are kept as a permanent record by the user of the fingerprint kit.

DETAILED DESCRIPTION OF THE DRAWINGS

Figure 1:
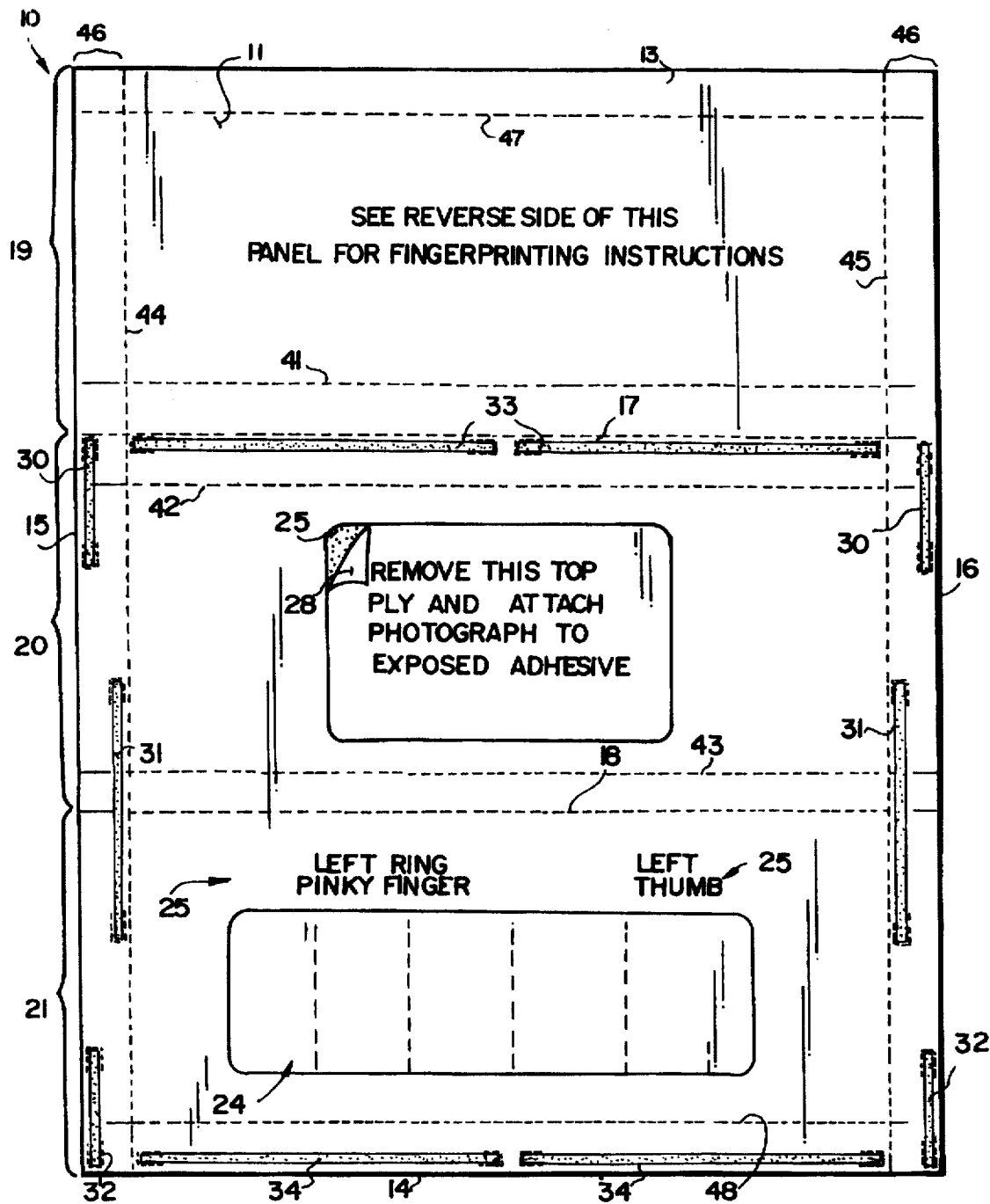
FIG. 1 is a top plan view of an exemplary quadrate paper sheet utilizable to make a self-contained fingerprint kit according to the present invention.
Figure 2:
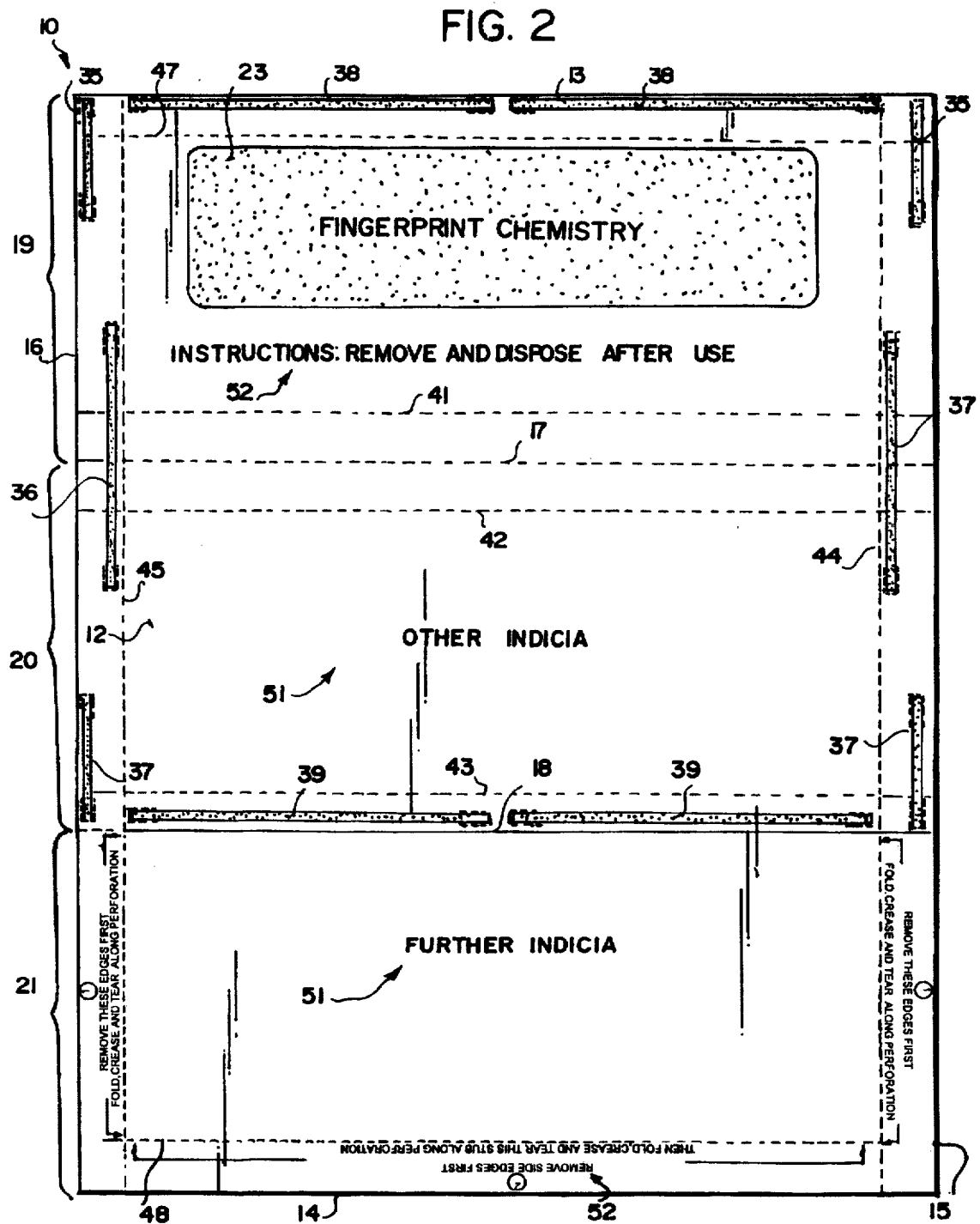
FIG. 2 is a bottom plan view of the sheet of FIG. 1.

An exemplary substantially quadrate sheet of paper according to the present invention (utilized to make a self-contained fingerprint kit according to the present invention) is shown generally by reference numeral 10 in FIGS. 1 and 2. The sheet 10 preferably is of bond paper or like cellulose stock, e.g. having a weight that is substantially the same as, or slightly greater than, bond paper used in conventional Z-folded mailers from Moore Business Forms, Inc. of Lake Forest, Ill., such as shown in U.S. Pat. Nos. 5,253,798 and 5,314,110 (the disclosures of which are hereby incorporated by reference herein). In the preferred exemplary embodiment illustrated in FIGS. 1 and 2 the sheet 10 is shown having dimensions that are approximately 8½×11 inches, for ease of construction, however it should be understood that almost any size may be utilized including A4, legal size, or specially cut sizes.

The sheet 10 has substantially parallel and opposite first and second major faces 11 (FIG. 1) and 12 (FIG. 2), respectively. It also has first and second substantially parallel end edges 13, 14, and first and second substantially parallel side edges 15, 16, which are substantially perpendicular to the end edges 13, 14.

The sheet 10 includes at least first and second lines of weakness 17, 18 that are substantially parallel to the end edges 13, 14 and separate the sheet 10 into at least first, second and third panels 19, 20, 21, respectively. Depending upon the particular information or accessory elements to be provided and the fingerprint kit to be constructed from the sheet 10, and the size of the sheet, four or even more panels similar to the panels 19–21 may be provided. The lines of weakness 17 preferably are perforation lines although they may comprise any conventional lines of weakness, such as fold lines, crease lines, die cut lines, score lines, or the like.

The sheet 10 also includes first dry fingerprint chemical, shown schematically at 23 in FIG. 2, disposed on a second face 12 and a fingerprint receiving area—illustrated at 24 in FIG. 1—on the first face 11. The invention is not restricted to any particular fingerprint chemical chemistry. For example, the area 24 may not have any chemical at all thereon but merely be a defined area for placement of fingerprints in a particular manner, and may include indicia—as illustrated schematically at 25 in FIG. 1—, or may comprise a second dry chemical cooperating with the first chemical 23 when applied thereto by a human finger to develop a fingerprint. The fingerprint chemical 23 (and the second chemical applied at 24) is preferably coated on the paper sheet 10, or a protective coating may be applied to the paper first before the fingerprint chemical 23 (24) is applied. One example that the fingerprint chemical chemistry may take is commercially available dry (inkless) chemical available from Scott Company of Flower Mound, Tex. With this chemistry a user wets his or her finger and then brings the finger into contact with the first dry chemical 23, which is water soluble and transfers to the finger. Then the finger is placed appropriately on the second chemical 24, reacting with the second chemical to develop a fingerprint.

The sheet 10 also preferably comprises a pressure sensitive adhesive area, seen at reference numeral 27 in FIG. 1, which may be a completely continuous or discontinuous (e.g patterned) area, but in any event is covered by a release sheet or ply 28 (e.g. having a silicone coating where contacting the adhesive 27) so that the sheet 28 may be readily removed to expose the adhesive 27. The adhesive area 27 is large enough to receive a photograph thereon (preferably of the face, head, and shoulder area of the same person whose fingerprints will be placed in the area 24), and may have the relative dimensions illustrated in FIG. 1 assuming that the sheet 10 is an 8½×11 inch standard sheet. The adhesive 27 may be any conventional pressure sensitive adhesive, and preferably is a permanent pressure sensitive adhesive although under some circumstances it may be removable or repositional adhesive.

While the locations of the components 23, 24, 27 may vary, in the preferred embodiment of the sheet 10 according to the present invention they are placed in the positions illustrated in FIGS. 1 and 2.

Figure 3:
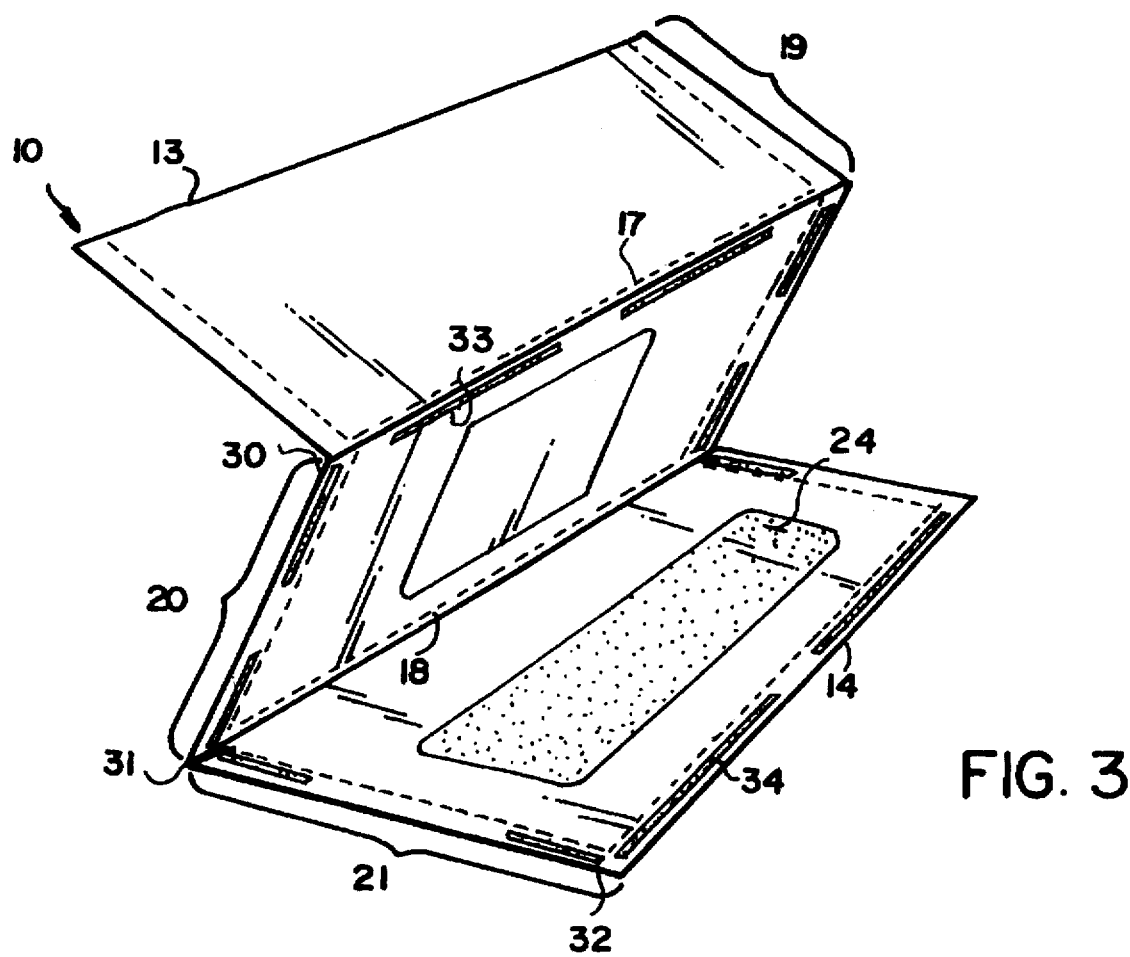
FIG. 3 is a top perspective view illustrating folding of the sheet of FIGS. 1 and 2 to form a self-contained fingerprint according to the present invention

The sheet 10 also preferably includes adhesive which is used to join the panels 19–21 together to provide a closed, self-contained, fingerprint kit when the panels 19–21 are Z-folded with respect to each other, as illustrated in FIG. 3. The panel joining adhesive is any suitable adhesive which can be sealed without in any way adversely affecting the fingerprint chemicals 23, 24 or the adhesive 27. In the preferred embodiment the adhesive for joining the panels 19–21 together is pressure sensitive adhesive or coadhesive such as used in Moore Business Forms, Inc. commercial pressure seal mailer type business forms, such as disclosed in U.S. Pat. No. 5,314,110. This allows the sheet 10 to be Z-folded (or in some instances C-folded) and to be sealed by using narrow width rollers which merely engage those portions of the sheet 10 which contain the panel joining adhesive, so that there is no heat or moisture or other extraneous environmental elements that might adversely affect the chemicals 23, 24 or the adhesive 27.

While a wide variety of different patterns and configurations of adhesive may be utilized, preferably the panel joining adhesive is positioned and configured as illustrated in FIGS. 1 and 2, including the strips (or other patterns) 30 disposed on the first face 11 of the panel 20 adjacent the side edges 15, 16, the strips 31 disposed on the face 11 spanning the panels 20, 21 and adjacent but spaced from the side edges 15, 16, the strips 32 disposed on the face 11 of the panel 21 adjacent the side edges 15, 16 and adjacent the end edge 14, the strips 33 disposed on the face 11 of panel 20 adjacent the line of weakness 17, the strips 34 disposed on the face 11 of the panel 21 adjacent the edge 14, the strips 35 disposed on face 12 adjacent the edges 15, 16 and adjacent the end edge 13; the strips 36 disposed on the face 12 spanning the panels 19, 20 and adjacent but spaced from the side edges 15, 16; the strips 37 disposed on the face 12 of the panel 20 adjacent the side edges 15, 16 and adjacent the perforation line 18; the strips 38 disposed on the face 12 of the panel 19 adjacent the end edge 13, and the strips 39 disposed on the face 12 of the panel 20 and adjacent the perforation line 18.

Additional lines of weakness are also provided so that when the sheet 10 is used (after all of the panel joining adhesive patterns 30–39 have been sealed) all of the interior components of the kit are readily accessible. For example, the additional perforation lines 41, 42 are provided straddling and substantially parallel to the first line of weakness 17, the perforation lines (or other lines of weakness) 43 formed in the panel 20 parallel to and on the opposite side of the adhesive strips 39 from the perforation line 18, and the perforation lines (or other lines of weakness) 44, 45 spaced from but adjacent the side edges 15, 16, respectively, and on the opposite side of the strips 30–32 and 35–37 from the side edges 15, 16, respectively. In this way the panel joining adhesive strips 30–32 and 35–37 are provided in removable end strips 46 which are detached by tearing along the perforation lines 44, 45, and similarly when there is detachment along the perforation lines 41–43 the panels so formed are free of panel joining adhesive. Other lines of weakness 47, 48, on the opposite sides of the strips 38 and 34, respectively, from the end edges 13, 14, also are preferably provided.

Figure 4:
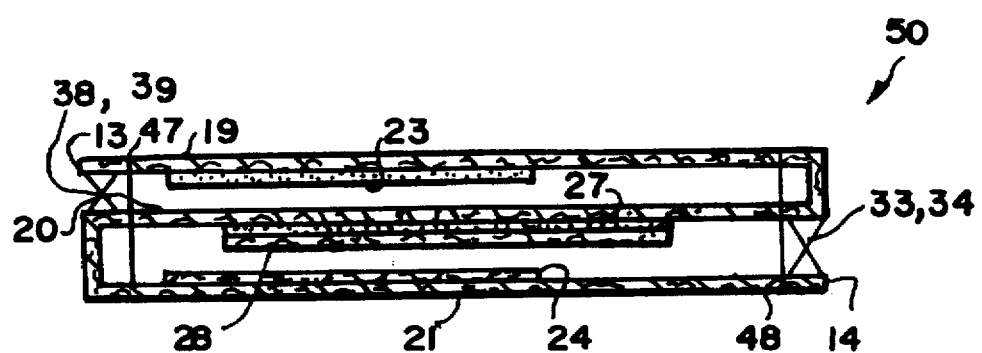
FIG. 4 is an end schematic view of a self-contained fingerprint kit according to the invention after folding of the sheet as indicated in FIG. 3, and with the end adhesive portion removed for clarity of illustration.

FIG. 3 shows the sheet 10 being Z-folded to bring the various adhesive strips into engagement with each other to be sealed (e.g. the strips 30 engaging the strips 32, the portions of the strips 31 on opposite sides of the panels 20, 21 engaging each other, the strips 34 engaging the strips 33, the strips 35 engaging the strips 37, the strips 38 engaging the strips 39, and the portions of the strips 36 on the opposite sides of the panels 19, 20 engaging each other), and then the sheet 10 is run through conventional narrow roller pressure sealing equipment such as available from Moore Business Forms, Inc. of Lake Forest, Ill., and such as shown in U.S. Pat. Nos. 5,169,489 and 5,397,427. The self-contained fingerprint kit produced as illustrated schematically at 50 in FIGS. 4 and 5 may have a wide variety of other indicia associated therewith depending upon the particular use to be put thereto, including promotional graphics such as illustrated schematically at 51 in FIG. 2, as well as instructional indicia as illustrated at 52 in FIG. 2.

The kit 50 may be utilized in a wide variety of environments, for example, provided as a promotional item such as in a box of cereal 54 (see FIG. 5). Since the fingerprint chemical 23, 24 is substantially completely sealed within the kit 50, the kit 50 may be safely disposed in the cereal box 54 either between the cardboard box and the interior plastic wrap, or even within the plastic wrap itself, since there would be no "leakage" or migration of the fingerprint chemical into the food contents of the box 54. Of course, other food boxes or other products (such as batteries, razors, or other consumer products) may include fingerprint kits 50 packaged as promotional items therein, but the kits 50 may be sold themselves packaged one or more within an external package.

FIG. 6 illustrates the components of the kit 50 that are permanently saved by the user. When the kit 50 is removed from the box 54 and the panels 19–21 are separated from each other by tearing along the perforation lines 44, 45, 47, 48, 41, 42, 18, etc. just the main bodies of the panels 19–21 remain. Where the particular fingerprint chemistry from Scott Company, as described above, is utilized, the user will then wet his or her finger, bring it in contact with the water soluble fingerprint chemical 23 on the panel 19, and then bring it into contact with the appropriate second dry chemical 24 portion (e.g. having indicia 25 associated with that finger of the user). After all the desired fingerprints have been applied to the area 24, the panel 19 is discarded. Also, the user removes the release liner 28 from the pressure sensitive adhesive 27, and presses a photograph 55 (see FIG. 6) of the person whose fingerprints are provided in the area 24, over the pressure sensitive adhesive 27. Panels 20, 21 are then retained together (e.g. stapled together, and placed in an envelope, and in a safe place.

It will thus be seen that according to the present invention a very simple, easy to use, versatile, inexpensive, yet effective self-contained fingerprint kit, and paper sheet for forming the fingerprint kit, have been provided. While the invention has been herein shown and described in what is presently conceived to be the most practical and preferred embodiment thereof, it will be apparent to those of ordinary skill in the art that many modifications may be made thereof within the scope of the invention (e.g. by utilizing a different substrate for sheet 10 aside from cellulose stock, such as plastic stock, or other materials), so that the invention is accorded the broadest interpretation of the appended claims so as to encompass all of the known structures, products, and devices.

What is claimed is:

1. A self-contained fingerprint kit, comprising:
   first, second and third panels, each having a top face and a bottom face, and connected to each other by lines of weakness so that said panels are readily separable from each other;
   panel joining adhesive for holding said panels together so that said top face of said second panel engages said bottom face of said first panel, and said bottom face of said second panel engages said top face of said third panel, said panels substantially parallel to each other;
   a first dry fingerprint chemical disposed in an area provided on one of said first panel bottom face or said second panel top face; and
   a fingerprint application area provided on said second panel bottom face, or said third panel top face, for receipt of fingerprints with fingerprint chemical transferred from said first dry fingerprint chemical, said fingerprint application area comprising a second dry fingerprint chemical disposed thereon, said first and second fingerprint chemicals cooperating to provide a developed fingerprint.

2. A self-contained fingerprint kit as recited in claim 1 wherein said first dry fingerprint chemical area is disposed on said first panel bottom face, and said second dry fingerprint chemical area is disposed on said third panel top face.

3. A self-contained fingerprint kit as recited in claim 2 further comprising a photograph-receiving pressure sensitive adhesive on said second panel bottom face, and a release liner covering said adhesive area, said adhesive area large enough to mount a photograph thereon.

4. A self-contained fingerprint kit as recited in claim 3 wherein said panels are quadrate and of substantially the same size, having aligned end edges and side edges; and wherein said panel joining adhesive comprises pressure sensitive adhesive or coadhesive along at least some of said aligned edges, and separated from said first and second fingerprint chemical areas and said photograph-receiving adhesive area by lines of weakness.

5. A self-contained fingerprint kit as recited in claim 1 wherein said panels are formed from a single substantially 8.5×11 inch sheet of bond paper.

6. A self-contained fingerprint kit as recited in claim 5 disposed within, and in combination with, a box of cereal.

7. A self-contained fingerprint kit as recited in claim 1 wherein said first dry fingerprint chemical is disposed on said first panel bottom face, and said fingerprint receiving area is disposed on said third panel top face.

8. A self-contained fingerprint kit as recited in claim 7 further comprising a photograph-receiving pressure sensitive adhesive on said second panel bottom face, and a release liner covering said adhesive area, said adhesive area large enough to mount a photograph thereon.

9. A specialty sheet comprising:
- a substantially quadrate sheet of paper having substantially parallel and opposite first and a second major faces, first and second substantially parallel end edges, and first and second substantially parallel side edges substantially perpendicular to said end edges;
- at least first and second lines of weakness substantially parallel to said end edges and separating said sheet into at least first, second, and third panels;
- a first dry fingerprint chemical disposed on said second face in said first panel; and
- a fingerprint receiving area disposed on said first face in said third panel, and said fingerprint receiving area comprising a second dry fingerprint chemical cooperating with said first chemical when applied thereto by a human finger to develop a fingerprint.

10. A sheet of paper as recited in claim 9 wherein said panels are of substantially the same size; and further comprising a photograph receiving adhesive area provided on said first face in said second panel, and a release sheet covering said photograph receiving adhesive area.

11. A sheet of paper as recited in claim 9 further comprising third and fourth lines of weakness substantially parallel to adjacent said first and second side edges to define marginal areas; and further comprising pressure sensitive adhesive or coadhesive disposed in said marginal areas.

12. A self-contained fingerprint kit, comprising:
- first, second and third panels, each having a top face and a bottom face;
- a first dry fingerprint chemical disposed in an area provided on one of said first panel bottom face or said second panel top face; and
- a fingerprint application area provided on said second panel bottom face, or said third panel top face, comprising a second dry fingerprint chemical disposed thereon, said second chemical for cooperating with said first chemical when applied thereto by a human finger to develop a fingerprint.

13. A self-contained fingerprint kit as recited in claim 12 further comprising a photograph-receiving pressure sensitive adhesive on said second panel bottom face, and a release liner covering said adhesive area, said adhesive area large enough to mount a photograph thereon.

14. A self-contained fingerprint kit, comprising:
- first, second and third panels, each having a top face and a bottom face;
- panel joining adhesive for holding said panels together so that said top face of said second panel engages said bottom face of said first panel, and said bottom face of said second panel engages said top face of said third panel, said panels substantially parallel to each other;
- a first dry fingerprint chemical disposed in an area provided on one of said first panel bottom face or said second panel top face;
- a fingerprint application area provided on said second panel bottom face, or said third panel top face, for receipt of fingerprints with fingerprint chemical transferred from said first dry fingerprint chemical;
- said first dry fingerprint chemical disposed on said first panel bottom face, and said fingerprint receiving area disposed on said third panel top face; and
- a photograph-receiving pressure sensitive adhesive on said second panel bottom face, and a release liner covering said adhesive area, said adhesive area large enough to mount a photograph thereon.

15. A self-contained fingerprint kit as recited in claim 14 wherein said panels are quadrate and of substantially the same size, having aligned end edges and side edges; and wherein said panel joining adhesive comprises pressure sensitive adhesive or coadhesive along at least some of said aligned edges, and separated from said first fingerprint chemical area, said fingerprint receiving area, and said photograph-receiving adhesive area, by lines of weakness.

16. A self-contained fingerprint kit as recited in claim 14 wherein said panels are formed from a single substantially 8.5×11 inch sheet of bond paper, and wherein said first dry fingerprint chemical is water soluble.

17. A self-contained fingerprint kit as recited in claim 14 disposed within, and in combination with, a box of cereal.

18. A specialty sheet comprising:
- a substantially quadrate sheet of paper having substantially parallel and opposite first and second major faces, first and second substantially parallel end edges, and first and second substantially parallel side edges substantially perpendicular to said end edges;
- at least first and second lines of weakness substantially parallel to said end edges and separating said sheet into at least first, second, and third panels;
- a first dry fingerprint chemical disposed on said second face;
- a fingerprint receiving area disposed on said first face, and comprising a second dry fingerprint chemical cooperating with said first chemical when applied thereto by a human finger to develop a fingerprint.

19. A sheet of paper as recited in claim 18 wherein said first dry fingerprint chemical is water soluble and wherein said sheet of paper is bond paper.

* * * * *